United States Patent [19]

Ron

[11] 4,404,186

[45] Sep. 13, 1983

[54] VACCINES OBTAINED FROM BACTERIAL MUTANT STRAINS

[75] Inventor: Eliora Z. Ron, Tel Aviv, Israel

[73] Assignee: Ramot University Authority for Applied Research and Industrial Development Ltd., Tel-Aviv, Israel

[21] Appl. No.: 245,954

[22] Filed: Mar. 20, 1981

[30] Foreign Application Priority Data

Mar. 9, 1980 [IL]  Israel ..................................... 59663

[51] Int. Cl.³ ..................... A61K 39/108; C12N 1/20; C12N 15/00; C12N 13/00
[52] U.S. Cl. ........................................ 424/92; 424/93; 435/172; 435/173; 435/253
[58] Field of Search .................... 424/92, 93; 435/172, 435/253

[56] References Cited

U.S. PATENT DOCUMENTS 3,907,987  9/1975  Wilson .................................. 424/92
3,975,517  8/1976  Wilson .................................. 424/92
4,311,797  1/1982  Khochatourians .................. 424/92

OTHER PUBLICATIONS

Metzler, D., Biochemistry, The Chemical Reaction of Living Cells, pp. 945–946, Academic Press, New York, 1977.

Lamanna, C., and Mallette, M., Basic Biology, Williams and Wilkens Co., Baltimore, 1915.

*Primary Examiner*—Blondel Hazel
*Attorney, Agent, or Firm*—Browdy & Neimark

[57] ABSTRACT

The present invention relates to a live vaccine for the vaccination of poultry and mammals against a variety of gram negative pathogens belonging to Enterobacteriaceae, comprising a bacterial deletion mutant derived from a non-pathogenic strain of *E. coli;* to a process for obtaining bacterial mutant strain for use in a live vaccine according to claim 1, which comprises exposing a non-pathogenic strain of *E. coli* to a mutation inducing agent and selecting strains devoid of O-antigens, and cultivating same to obtain the bacteria for use in such live vaccine; to the novel mutant strain *E. coli* LR-2, and to a process for immunizing poultry and mammals against Enterobacteriaceae which comprises applying to the avian or to the mammal an effective dose of such a vaccine by oral route or as aerosol.

5 Claims, No Drawings

VACCINES OBTAINED FROM BACTERIAL MUTANT STRAINS

FIELD OF THE INVENTION

The present invention relates to novel bacterial mutants, to a process for producing same and to live vaccines containing same. The invention relates to "broad spectrum vaccines" based on novel bacterial mutant strains, and to a process of vaccination of mammals and poultry by means of such live vaccine. The vaccine is of special value in animal husbandry and provides a (long-lasting) immunization against a wide range of bacteria. The novel mutants are non-reverting; they are substantially non-pathogenic and can be used for the efficient immunization of mammals and poultry.

BACKGROUND OF THE INVENTION

Gram negative bacteria, and especially bacteria belonging to the Enterobacteriaceae (enteric bacteria) constitute an increasingly serious problem in medicine and in animal husbandry. The bacteria of this kind cause various infections in poultry, in humans, and in other mammals, and the treatment of the diseases and infections caused by same are becoming hard to treat due to the fact that a large part of such bacteria have developed resistance to a large part of antibiotics presently in use. This resistance to antibiotics is probably due to the fact that such bacteria carry infective drug resistance plasmids.

A possible solution to the problems caused by such bacteria, and especially in the field of animal husbandry (such as breeding of poultry and the like) is the use of effective vaccinations. Such vaccinations ought to be long-lasting and ought to cover a large spectrum of infective agents. Since Enterobacteriaceae belong to a large variety of serotypes, it is hard to prepare a vaccine which will cover a sufficient number of infective agents.

It has been shown in laboratory experiments that it is possible to obtain bacterial mutants which lack the O-antigen, i.e. bacteria which can be defined as "deep rough" and that such bacteria have a spectrum of immunization, when used in heat-killed vaccines, which is quite broad. Such bacterial mutants, i.e. "deep rough" bacteria can be used as heat-killed vaccines for the immunization against a quite wide range of Enterobacteria, but immunization by means of heat-killed vaccines is not very effective: a plurality of immunization is required, which must be administered by injection. Furthermore, such immunization is of short duration only. Immunization by injection is not convenient in human medicine, and practically prohibitive in animal husbandry when large numbers of poultry or the like have to be vaccinated. The drawbacks of conventional vaccines and also of heat-killed vaccines of the "deep rough" type bacteria are overcome by the present invention.

SUMMARY OF THE INVENTION

The present invention relates to novel bacterial mutants which can be used for the effective vaccination of poultry and mammals. The invention relates to a process for the preparation of such mutant strains and to vaccines based on live mutant bacteria thus produced. It further relates to novel vaccines based on such live bacteria, and to a process of vaccination of livestock by means of such vaccines.

By preparing "deep rough" mutants of predetermined bacteriae, there can be produced an isolated novel strains which completely lack the O-antigen. Such strains can also be obtained which carry a non-reverting mutation in the biosynthesis of lipopolysaccharides. The mutants are deletion mutants and can be cultivated in a convenient manner. No reversions were observed in the laboratory or after re-isolation from injected animals. The strains are substantially non-virulent and non-pathogenic. High numbers of such bacteria were injected into laboratory animals without causing any harmful effects. Such mutants are the effective active constituents of live vaccines which provide a wide spectrum of protection against pathogens, the scope of the protection being a function of the type of bacteria used.

According to a specific embodiment of the invention there are provided deletion mutants of Enterobacteriaceae which substantially lack the O-antigen (i.e. can be defined as "deep rough"), and which are adapted to provide an efficient and long lasting immunization against a wide range of bacteria which belong to such Enterobacteriaceae. The novel vaccines can be used in medicine. They are of special value in animal husbandry. It is one of the pronounced advantages of such live vaccines that they can be administered as aerosols. Experiments have shown that chicks immunized by exposure to an aerosol of such a vaccine acquired a long-lasting protection against a wide spectrum of avian pathogens.

A preferred embodiment of the invention relates to a novel mutant strain of *Escherichia coli* K-12, which by itself is a non-pathogenic strain and in which it is allowed to perform recombinant DNA experiments—'EKl'. The novel mutants are substantially non-virulent and can be used in live vaccines. Such vaccines can be used in the form of aerosols for effective immunization of mammals. The novel strain is a mutant lacking the O-antigen as a result of a non-reverting deletion. Since such O-antigens are responsible for species specific sero-types, a mutant which is defective in the biosynthesis of the O-antigens brings about immunization to those antigens which are common to all the enteric bacteria, i.e. the KDO and lipid A. The mutant is effective in providing an effective immunization against a wide range of Enterobacteriaceae. The novel mutant of the K-12 strain is termed LR-2. It is characterized further on.

The mutagenesis was effected by the use of nitrous acid, and by selection of the desired mutant strain. The strain is non-reverting, the rate of reversion being less than $10^{-11}$. No revertants were isolated after repeated injections into animals. Mutagenesis can be induced by radiation, phage induced deletions such as phage $\mu$, etc.

The invention is applicable to a wide range of bacteria. It is illustrated by way of example in the following reference to the production of a specific novel mutant strain derived from *Escherichia coli* K-12.

Preparation of Mutant Strain

Mutagenesis was effected with nitrous acid which was prepared just before use by mixing equal quantities of sodium nitrate (0.1 M) and 0.1 M acetate buffer, pH 4.6 to a final concentration of 0.05 M respective the nitrite. A single colony of *Escherichia coli* K-12 grown overnight with shaking at 37° C. in a nutrient Medium LB containing 10 g Bacto trypton, 5 g yeast extract and 10 g sodium chloride per liter, was washed with an equal volume of acetate buffer and resuspended in 0.3 ml of nitrous acid (0.05 M). After incubation during 10 minutes at 37° C. the cells were washed, resuspended in 10 ml of Medium LB and incubated overnight at 37° C.

The mutant was screened as follows: Overnight culture was diluted 1:100 into fresh LB medium, and grown at 37° C. with shaking. After growth has resumed bacteriophage T4 was added at a multiplicity of infection of 5 and incubation continued until lysis has occurred. Th surviving bacteria were placed on LB agar plates and colonies were screened for antibiotics sensitivity and phage resistance.

The novel mutant, designated as LR-2, has the following characteristics:

Nutrients required:

Leucine, adenine, tryptophane, histidine, arginine, isoleucine, valine, methionine, thiamine.

The strain does not ferment the following:

Lactose, galactose, xylose, mannitol, maltose.

The strain is resistant to:

Coli phage $T_1$, Coli phage $T_4$, Coli phage $T_7$, Coli phage $P_1$. Sensitivity towards other phages was not tested and it is presumed that the strain is resistant to other Coli phages.

Highly sensitive towards:

Crystal violet, gentian violet, methylene blue, eosin and other dyes; high molecular weight (hydrophobic) antibiotics: novobiocin, rifampicin, erythromycin and the like.

The microorganism was deposited with the German Collection Microorganisms (DSM), Goettingen, and given the accession number DSM 2051.

The reversion rate was tested and was found to be less than $10^{-11}$: No revertants were isolated on plates and after multiple injection to animals. It is believed likely that the mutant which blocks formation of O-antigen is a deletion. The method of induction of mutation used is one known to produce a high yield of deletions.

Chemical analysis of purified lipopolysaccharide from strain LR-2 has proved that the mutant contains lipid A and KDO; no O-antigen carbohydrates could be detected.

Production of Vaccine

For the production of the vaccine a single colony of the LR-2 strain was grown overnight on LB medium and diluted 1:100 in the same medium for large volumes. Cells were harvested at about $5 \times 10^8$ bacteria per ml, washed 3 times by centrifugation in 1% sodium chloride and resuspended in the same solution. At this stage it was possible to lyophilize the culture and to obtain a highly efficient live vaccine.

Immunization

Mice and chicks were injected with $10^9$ living bacteria per animal. There were no adverse reactions and the rate of survival was 100%. Mice were injected with a vaccine containing $10^7$ bacteria per mouse (i.p. injections), and this resulted in a protection lasting for more than 2 weeks against lethal doses of *K.pneumonia* which was injected i.p. A titer of 1:640 in hemaglutination was obtained after 6 i.p. injections.

Antibodies formed after 6 injections cross-react with lipopolysaccharide (LPS) from *E. coli* 075, *K.Pneumonia*, and *Enterobacter aerogenes*.

Six injections (i.p.) of $10^7$ bacteria each provide an effective immunization against the i.v. injection of lethal doses of *E.coli* 075 (see Table 3).

Test for Virulence

Chicks (1, 7, 14 and 28 days of age) were exposed to large doses of the vaccine. A quantity of $10^8$ bacteria was introduced directly into the air sac of the chicks or injected i.p. and no harmful effects were apparent.

Various laboratory animals (mice, rats) were injected with a high number (more than $10^9$ per animal), and no harmful effects were observed. The live vaccine is safe and non-pathogenic and can be used for the vaccination of mammals and poultry without any harmful side effects.

Immunization of Chicks

Chicks were immunized by an exposure to an aerosol of a vaccine containing $3 \times 10^8$ bacteria per milliliter. A quantity of 10 ml was aerosolized into a volume of 20 liters in which 36 chicks were present and these were exposed to this aerosol during 10 minutes.

Another run was carried out by applying the vaccine in drinking water. In this run a quantity of $3 \times 10^8$ bacteria/ml was provided.

A third run was carried out by injection into the air sac of $2 \times 10^8$ bacteria per chick.

The results are summarized in Table 1. The immunized chicks were exposed to *E.coli* $O_2$ and to *E.coli* $O_{78}$ which are avian pathogens.

TABLE 1

PROTECTION OF CHICKS BY VACCINATION WITH LR-2 AGAINST CHALLENGE (INJECTION INTO AIR SAC) WITH *E. coli* $O_2$ The challenge was with $10^4$ bacteria applied into the air sac. There were 20 chicks in each group.

| | Age at Immunization (days) | Method of Immunization | Age at challenge | % weight increase |
|---|---|---|---|---|
| I. | 1 + 7 | spray, spray | 28 | 50.5 |
| | 1 + 7 | spray, drinking water | 28 | 57.6 |
| | 1 + 7 | control | 28 | 20.4 |
| II. | 1 + 7 | spray, spray | 30 | 12 |
| | 1 + 7 | control | 30 | −3 |

TABLE 2

PROTECTION OF CHICKS BY VACCINATION WITH LR-2 AGAINST CHALLENGE WITH *E. coli* $O_{78}$ The immunization was by exposure to an aerosol, $3 \times 10^8$/ml 10 ml in a 20 liter volume during 10 minutes. Groups of 20 chicks were used.

| | Age at Immunization (days) | Age at challenge (days) | Weight increase after challenge (%) |
|---|---|---|---|
| I. | 1 + 14 | 30 | 5.7 |
| | 1 + 21 | 30 | 9.2 |
| | 21 | 30 | 11.3 |
| | control | 30 | 0.02 |
| II. | 1 + 21 | 50 | −6 |
| | 1 + 14 + 40 | 50 | 6.9 |
| | 40 | 50 | 6.1 |
| | control | 50 | −5 |

The challenge was with $10^5$ bacteria applied into the air sac. Mice were immunized by 6 vaccinations, i.p. of $2 \times 10^7$ live bacteria during 2 weeks and a booster was given i.p. at week 3 and at week 4. The challenge was given at the end of the 6th week.

TABLE 3

| SURVIVORS AFTER CHALLENGE WITH *E. coli* $O_{75}$ ($2 \times 10^7$, i.v.) | | |
|---|---|---|
| Immunization with | | |
| *E. coli* O 75 (heat killed) | 17/18 | 94% |
| LR-2 | 22/31 | 70% |
| *P. aureginosa* (heat killed) | 12/38 | 31% |
| NaCl (1%), control | 12/36 | 33% |

The process of inducing mutation set out above can be used with a variety of similar bacteria (such as for example other members of Enterobacteriaceae and Pseudomonas) and the resulting mutants which are devoid of O-antigen can be used for the wide-spectrum immunization of mammals in the form of a live vaccine. Immunization by application of an aerosol of the vaccine is a very convenient and effective route of immunization by this type of vaccine.

Polyvalent Vaccine

Immunization with LR-2 protects mice against challenge with a wide range of ENTEROBACTERIACEAE.

| Day of Immunization | Organism used for challenge | Day of challenge | % Survivors |
|---|---|---|---|
| 1 | *K. pneumonia* | 7 | 100 |
| 1 | " | 14 | 0 |
| 1,7 | " | 21 | 90 |
| 1,7 | " | 28 | 20 |
| 1,7,14,21 | " | 42 | 30 |
| Control | " | | 0 |
| 1 | *P. Vulgaris* | 7 | 100 |
| 1 | " | 14 | 0 |
| 1,7 | " | 21 | 100 |
| Control | " | | 0 |

Both immunization and challenge were i.p. in $C_3HeB$ mice. Immunization—$2\times10^7$ bacteria per mouse, challenge—$2LD_{50}$.

I claim:

1. A live vaccine for the vaccination of poultry and mammals against variety of gram negative pathogens belonging to Enterobacteriaceae, comprising a bacterial deletion mutant *E. coli* LR-2 derived from a non-pathogenic strain of *E. coli,* and a carrier therefor.

2. A live vaccine according to claim 1 wherein said carrier is a suitable liquid carrier.

3. Man-made artifically substantially pure mutant strain *E. coli* LR-2, accession no. DSM 2051.

4. A process for immunizing poultry and mammals against Enterobacteriaceae which comprises applying to the avian or to the mammal an effective dose of a vaccine according to claim 1, by oral route or as aerosol.

5. A process according to claim 4, wherein the vaccine is applied to poultry.

* * * * *